United States Patent
Isaji et al.

(10) Patent No.: US 9,694,027 B2
(45) Date of Patent: *Jul. 4, 2017

(54) PYRAZOLE DERIVATIVE AND USE THEREOF FOR MEDICAL PURPOSES

(71) Applicant: KISSEI PHARMACEUTICAL CO. LTD., Matsumoto-shi, Nagano (JP)

(72) Inventors: Masayuki Isaji, Azumino (JP); Masaaki Takemura, Azumino (JP); Hidetoshi Isawa, Joetsu (JP); Yukihiko Hotei, Azumino (JP); Itaru Miyashita, Tokyo (JP)

(73) Assignee: KISSEI PHARMACEUTICAL CO., LTD., Nagano (JP)

( * ) Notice: Subject to any disclaimer, the term of this patent is extended or adjusted under 35 U.S.C. 154(b) by 10 days.

This patent is subject to a terminal disclaimer.

(21) Appl. No.: 14/995,489

(22) Filed: Jan. 14, 2016

(65) Prior Publication Data

US 2016/0129031 A1    May 12, 2016

Related U.S. Application Data

(63) Continuation of application No. 14/399,093, filed as application No. PCT/JP2013/062755 on May 2, 2013, now Pat. No. 9,273,085.

(30) Foreign Application Priority Data

May 7, 2012 (JP) .................................. 2012-105847

(51) Int. Cl.
*A61K 31/7056* (2006.01)
*C07H 17/02* (2006.01)

(52) U.S. Cl.
CPC ......... *A61K 31/7056* (2013.01); *C07H 17/02* (2013.01)

(58) Field of Classification Search
None
See application file for complete search history.

(56) References Cited

U.S. PATENT DOCUMENTS

| 9,273,085 B2* | 3/2016 | Isaji .................... A61K 31/7056 |
| 2005/0272669 A1 | 12/2005 | Fushimi et al. |
| 2010/0279962 A1 | 11/2010 | Takeuchi et al. |
| 2011/0034679 A1 | 2/2011 | Takeuchi et al. |
| 2013/0085132 A1 | 4/2013 | Miura et al. |

FOREIGN PATENT DOCUMENTS

| WO | 2004/018491 A1 | 3/2004 |
| WO | 2009/084531 A1 | 7/2009 |
| WO | 2009/128421 A1 | 10/2009 |

OTHER PUBLICATIONS

International Search Report dated Jul. 16, 2013, issued in corresponding application No. PCT/JP2013/062755.
Hongo, Michio, et al., "Gastrointestinal Disorders in Diabetic Patients—Including Recent Findings", Diabetes Journal, Japan, 2003, vol. 31, No. 3, pp. 86-91, w/English translation.
Takagi, Makoto, "Peripheral Neuropathy: Its Pathology and Treatment in Practice: Types of Autonomic Nuropathy Observed in Diabetes", Modern Physician, Japan, 1998, vol. 18, No. 6, pp. 717-719, w/English translation.
Supplementary European Search Report dated Jun. 2, 2015, issued in corresponding European application No. EP 13 78 7714, (1 page).
Longstreth et al., "Functional Bowel Disorders", 2006, pp. 1480-1491, vol. 130, issue No. 5.

* cited by examiner

*Primary Examiner* — Traviss C McIntosh, III
(74) *Attorney, Agent, or Firm* — Westerman, Hattori, Daniels & Adrian, LLP

(57) ABSTRACT

The present invention provides pyrazole derivatives, uses thereof for medical purposes and so on. More particularly, the present invention relates to pharmaceuticals useful for the prevention or treatment of constipation, which comprise as an active ingredient 3-(3-{4-[3-(β-D-glucopyranosyloxy)-5-isopropyl-1H-pyrazol-4-ylmethyl]-3-methylphenoxy}propylamino)-2,2-dimethylpropionamide, or a pharmaceutically acceptable salt thereof. The pharmaceuticals of the present invention exert an effect of increasing the frequency of bowel movement or the like, and are useful for the prevention or treatment of constipation.

6 Claims, 1 Drawing Sheet

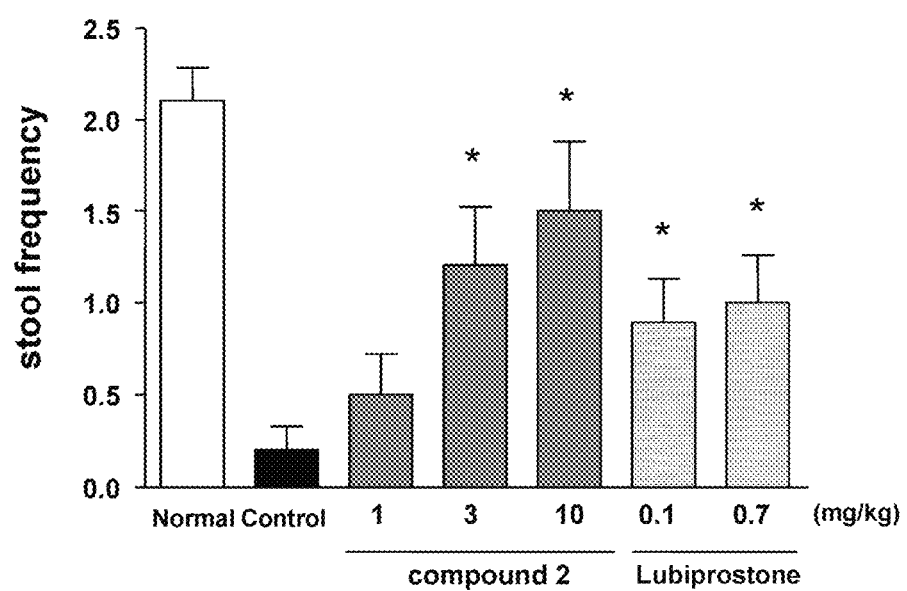

PYRAZOLE DERIVATIVE AND USE THEREOF FOR MEDICAL PURPOSES

This application is a Continuation of U.S. application Ser. No. 14/399,093, filed on Nov. 5, 2014, which is a National Stage of International Application No. PCT/JP2013/062755, filed on May 2, 2013, which claims priority to Japanese priority application No. 2012-105847 filed on May 7, 2012, which are hereby incorporated by reference.

TECHNICAL FIELD

The present invention relates to pharmaceuticals which are useful for the prevention or treatment of constipation.

More particularly, the present invention relates to pharmaceuticals which are useful for the prevention or treatment of constipation and which comprise as an active ingredient a compound (chemical name: 3-(3-{4-[3-(β-D-glucopyranosyloxy)-5-isopropyl-1H-pyrazol-4-ylmethyl]-3-methylphenoxy}propylamino)-2,2-dimethylpropionamide, hereinafter sometimes referred to as "Compound 1") represented by the formula:

[Chem. 1]

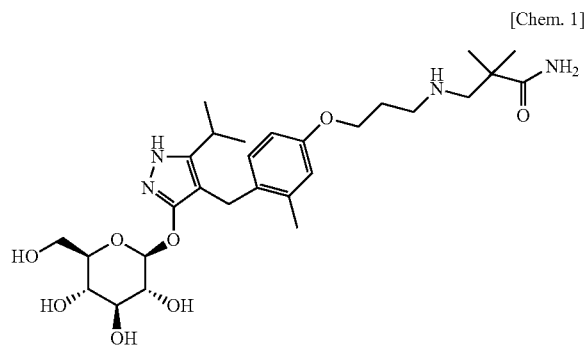 [SMILES: Cc1cc(OCCCNCC(C)(C)C(N)=O)ccc1Cc1c(O[C@@H]2O[C@H](CO)[C@@H](O)[C@H](O)[C@H]2O)n[nH]c1C(C)C]

or a pharmaceutically acceptable salt thereof.

BACKGROUND ART

Normally, bowel movement occurs habitually and dose not prevent someone from leading daily life. However, comfortable bowel movement of sufficient volume becomes difficult for some reasons and a condition associated with a physical suffering is caused. It is called constipation. Constipation is generally associated with straining during bowel movement, hard feces, decreased frequency of bowel movement, sensation of incomplete evacuation, bloating, prolonged transit time of food/stool in the entire gastrointestinal tract or colon and so on.

Constipation is classified into acute constipation and chronic constipation based on a period of medical history. In addition, constipation is classified into organic constipation and functional constipation based on its etiology. Organic constipation is a condition that it is difficult to defecate due to organic disorders such as stricture, obstruction and so on of gastrointestinal tract caused by colonic cancer, colonic polyps, uterine fibroid and so on. Furthermore, functional constipation is further classified into symptomatic constipation, drug-induced constipation and other constipation. Symptomatic constipation is constipation secondary to diseases other than gastrointestinal diseases. Drug-induced constipation is constipation which is secondarily caused by drugs, and it is known that it is caused by the administration of drugs which have an antimotility effect, such as opioid, anticholinergic drugs and the like. Functional constipation which is not symptomatic constipation or drug-induced constipation is the most common type, it is also called chronic idiopathic constipation (CIC), and it is caused by various reasons such as changes in eating habits and living environment, psychological factors and so on. Chronic constipation can be also classified into slow transit constipation and outlet obstruction based on reasons of constipation. Slow transit constipation is a condition in which the passage of the stool through the proximal colon to distal colon is impaired due to the decrease of colonic smooth muscle contraction, diminished peristalsis and the like, and outlet obstruction is a condition in which it is not possible to defecate due to impaired function of defecation even though the stool is transferred to rectum. Irritable bowel syndrome with constipation (IBS-C) is constipation in which gastrointestinal symptom dominated by abdominal pain, abdominal discomfort and stool abnormality is continued without organic changes in the gastrointestinal tract, and some patients of functional constipation may be classified as IBS-C (see Non-patent literatures 1-3).

The treatment of constipation includes life therapy, drug therapy, behavior therapy and surgical therapy. As the first choice in the treatment, life therapy involving a correction of irregular dietary habits, correction of bowel habits, and sufficient intake of high-fiber food and water is a basic treatment. Drug therapy is indicated in patients whose symptoms of constipation do not improve with life therapy.

In principle, drug therapy is initiated with drugs having a mild effect such as osmotic laxatives and bulk-forming laxatives which increase a volume of gut content. Irritant laxatives, prokinetic agents and the like are used when the effect of the above drugs is insufficient. Osmotic laxatives and bulk-forming laxatives are less addictive and can be administered for a long time. However, it is important to care for renal disorder, abnormal electrolyte level in the blood, hypermagnesemia of renal disorder or the like. In addition, it is known that addictions and inflammatory changes on intestinal mucosa may be caused by continued administration of irritant laxatives.

Lubiprostone is known as a new therapeutic agent for constipation (see Non-patent literature 4). Lubiprostone is sold as a therapeutic agent for chronic constipation (except for constipation due to organic diseases) in Japan. Lubiprostone is also sold as a therapeutic agent for chronic idiopathic constipation and irritable bowel syndrome with constipation, and is approved as a therapeutic agent for opioid-induced constipation (OIC) in the U.S.A.

Therefore, it is said that the drugs for the prevention or treatment of constipation are not sufficient now, and a drug for the prevention or treatment of constipation having a new mechanism of action, which causes fewer adverse reactions, has been strongly desired.

Compound 1 or a pharmaceutically acceptable salt thereof is known to be useful as an agent for the prevention or treatment of a disease associated with hyperglycemia such as diabetes, abnormal glucose tolerance, impaired fasting glucose, diabetic complication, obesity and so on (see Patent literatures 1-3).

However, it is not known that Compound 1 or a pharmaceutically acceptable salt thereof is useful as an agent for the prevention or treatment of constipation.

Patent literature 1: International publication No. WO2004/018491

Patent literature 2: International publication No. WO2009/084531

Patent literature 3: International publication No. WO2009/128421
Non-patent literature 1: Tetsuji Kitahora and 4 persons, *Bessatsu Nippon Rinsho Shinryouikibetsusyoukougun series,* 2009, Vol. 12, p. 422-427
Non-patent literature 2: Kouji Komori and 4 persons, *Bessatsu Nippon Rinsho Shinryouikibetsusyoukougun series,* 2009, Vol. 12, p. 433-435
Non-patent literature 3: George F. Longstreth et al, *Gastroenterology,* 2006, Vol. 130, p. 1480-1491
Non-patent literature 4: S. Fukudo et al, *Neurogastroenterology and Motility,* 2011, Vol. 23, p. 544-e205

DISCLOSURE OF THE INVENTION

Problems to be Solved by the Invention

A problem of the present invention is to provide pharmaceuticals and the like which are useful for the prevention or treatment of constipation.

Means for Solving the Problems

The present invention relates to pharmaceuticals for use in the prevention or treatment of constipation, which comprise as an active ingredient Compound 1, or a pharmaceutically acceptable salt thereof.

That is, the present invention relates to:

[1] a pharmaceutical for use in the prevention or treatment of constipation, which comprises as an active ingredient 3-(3-{4-[3-(β-D-glucopyranosyloxy)-5-isopropyl-1H-pyrazol-4-ylmethyl]-3-methylphenoxy}propylamino)-2,2-dimethylpropionamide, or a pharmaceutically acceptable salt thereof;

[2] the pharmaceutical as described in the above [1], which comprises as an active ingredient bis[3-(3-{4-[3-(β-D-glucopyranosyloxy)-5-isopropyl-1H-pyrazol-4-ylmethyl]-3-methylphenoxy}propylamino)-2,2-dimethylpropionamide]monosebacate;

[3] the pharmaceutical as described in the above [1] or [2], wherein the constipation is functional constipation;

[4] the pharmaceutical as described in the above [3], wherein the functional constipation is chronic idiopathic constipation;

[5] the pharmaceutical as described in the above [3], wherein the functional constipation is drug-induced constipation; and the like.

Effect of the Invention

The pharmaceuticals of the present invention exert an effect of increasing the frequency of bowel movement or the like, and are useful for the prevention or treatment of constipation.

BRIEF DESCRIPTION OF THE DRAWINGS

FIG. 1 shows the result of Example 1, which includes the frequency of bowel movement within 24 hours after the administration. In the FIGURE, each bar chart shows a value of Normal group (Normal), Control group (Control), the group administered with 1 mg/kg of Compound 2, the group administered with 3 mg/kg of Compound 2, the group administered with 10 mg/kg of Compound 2, the group administered with 0.1 mg/kg of lubiprostone, or the group administered with 0.7 mg/kg of lubiprostone from the left respectively. The vertical axes show the frequency of bowel movement (which is the frequency indicating bowel movement in the observation three times a day) (The data indicate the mean±standard error of 10 examples per group.). * shows a significant difference with the Control group.

MODE FOR CARRYING OUT THE INVENTION

As the pharmaceutically acceptable salt of Compound 1, an acid additive salt with a mineral acid such as hydrochloric acid, hydrobromic acid, nitric acid, phosphoric acid and the like, an acid additive salt with an organic acid such as formic acid, acetic acid, methanesulfonic acid, benzenesulfonic acid, p-toluenesulfonic acid, propionic acid, citric acid, succinic acid, tartaric acid, fumaric acid, butyric acid, oxalic acid, malonic acid, maleic acid, lactic acid, malic acid, carbonic acid, glutamic acid, aspartic acid, benzoic acid, sebacic acid, pamoic acid and the like, and so on can be illustrated. More preferably, monosebacate of Compound 1 (chemical name: bis[3-(3-{4-[3-(β-D-glucopyranosyloxy)-5-isopropyl-1H-pyrazol-4-ylmethyl]-3-methylphenoxy}propylamino)-2,2-dimethylpropionamide] monosebacate; hereinafter sometimes referred to as "Compound 2"), hemifumarate dihydrate of Compound 1 (chemical name: 3-(3-{4-[3-(β-D-glucopyranosyloxy)-5-isopropyl-1H-pyrazol-4-ylmethyl]-3-methylphenoxy}propylamino)-2,2-dimethylpropionamide hemifumarate dihydrate; hereinafter sometimes referred to as "Compound 3") and the like can be illustrated.

Compound 1 or a pharmaceutically acceptable salt thereof of the present invention also includes a solvate thereof with a pharmaceutically acceptable solvent (such as water, ethanol or the like).

Compound 1 or a pharmaceutically acceptable salt thereof of the present invention can be also prepared by a method described in patent literatures 1-3 or a similar method thereto.

Compound 1 of the present invention may be converted to a prodrug appropriately and be used. For example, a prodrug of Compound 1 can be prepared by introducing an appropriate group forming a prodrug into any one or more groups selected from a hydroxy group, an amino group and an amino group of the pyrazole ring of Compound 1 using a corresponding reagent to produce a prodrug such as a halide compound or the like in the usual way, and then by suitably isolating and purifying in the usual way as occasion demands. As a group forming a prodrug, for example, a group as described in "Development of medicine" 1990, Vol. 7, p. 163-198, published by Hirokawa shoten can be illustrated.

The pharmaceuticals of the present invention can be administered as various formulations which include oral forms, for example, such as tablets, capsules, granules, powders, fine granules, dry syrups and the like, and parenteral forms such as liquid forms, ointment forms, suppositories and the like.

The pharmaceuticals of the present invention can be prepared as various formulations by admixing or diluting/dissolving an active ingredient with an appropriate pharmaceutical carrier such us excipients, disintegrators, binders, lubricants, diluents, buffers, tonicity agents, preservatives, wetting agents, emulsifiers, dispersants, stabilizers, solubilization agents and the like using conventional methods.

The pharmaceuticals of the present invention can be also administered in combination with another drug which is used in the treatment of constipation. As another drug, for example, bulk-forming laxatives such as carmellose sodium and the like, osmotic laxatives such as magnesium oxide and the like, irritant laxatives such as sodium picosulfate hydrate and the like, enemas such as glycerin and the like, suppositories such as sodium hydrogen carbonate/anhydrous sodium dihydrogen phosphate and the like, tuning agents of gastrointestinal motility such as trimebutine maleate and the like, chloride channel activators such as lubiprostone and the like, guanylyl cyclase receptor agonists such as linaclotide and the like, μ-opioid receptor antagonists such as methylnaltrexone and the like, bile acid transporter inhibitors such as elobixibat and the like, serotonin 4 receptor agonists such as prucalopride and the like, and so on can be illustrated.

When the pharmaceuticals of the present invention are used in combination with the above drugs, the present invention includes all simultaneous administration as a single formulation, simultaneous administration as separate formulations by the same administration pathway or different pathways, and administration at different times as separate formulations by the same administration pathway or different pathways.

The dosage of an active ingredient of the present invention is appropriately decided depending on the body weight, age, sex, degree of disorders of each patient and the like. The dosage in an adult human can be decided within the range of, for example, 0.1 to 160 mg per day, 1 to 60 mg per day, 2 to 60 mg per day, 2 to 40 mg per day, 2 to 20 mg per day or 2 to 10 mg per day in the case of oral administration, and the daily dose can be divided into one, two or three times per day and administered.

In addition, for example, 1 mg once daily, 1 mg twice daily, 1 mg three times daily, 2 mg once daily, 2 mg twice daily, 2 mg three times daily, 2.5 mg once daily, 2.5 mg twice daily, 2.5 mg three times daily, 5 mg once daily, 5 mg twice daily, 5 mg three times daily, 10 mg once daily, 10 mg twice daily, 10 mg three times daily, 15 mg once daily, 15 mg twice daily, 15 mg three times daily, 20 mg once daily, 20 mg twice daily, 20 mg three times daily, 40 mg once daily, 40 mg twice daily, 80 mg once daily, or 80 mg twice daily can be administered.

Furthermore, the first dosage is selected from, for example, 1 mg, 2 mg, 2.5 mg, 5 mg, 10 mg or 20 mg, and then the dosage can be increased or decreased gradually depending on the sensitivity, the degree of disorders or the like of each patient.

The dosage can be decided within the range of, for example, 0.05 to 80 mg per day in the case of parenteral administration.

The pharmaceuticals of the present invention can be also administered before a meal, after a meal or with a meal, preferably administered after a meal.

In the present invention, functional constipation is constipation other than organic constipation among constipation. Chronic idiopathic constipation (CIC) is constipation other than symptomatic constipation and drug-induced constipation among functional constipation, and includes atonic constipation, spastic constipation, rectal constipation and the like.

Also, in the present invention, chronic constipation includes chronic organic constipation and chronic functional constipation. Therefore, chronic constipation includes chronic idiopathic constipation (CIC), symptomatic constipation, drug-induced constipation, irritable bowel syndrome with constipation (IBS-C) and chronic organic constipation.

Symptomatic constipation is constipation secondary to diseases other than gastrointestinal diseases among functional constipation, and includes constipation which is caused by endocrine diseases such as hypothyroidism, pheochromocytoma, hypopituitarism, hyperparathyroidism and so on, metabolic diseases such as amyloidosis, uremia and so on, poisonings such as lead poisoning, arsenic poisoning and so on, neurologic diseases such as Parkinson's disease, cerebrovascular disorder, brain tumor, multiple sclerosis and so on, connective tissue diseases such as scleroderma and so on, and anus diseases such as perianal abscess and so on, and the like.

Drug-induced constipation is constipation which is secondarily caused by drugs among functional constipation, and includes constipation which is caused by the administration of a drug having an antimotility effect such as opioid and so on, an anticholinergic drug and the like (for example opioid-induced constipation).

Irritable bowel syndrome with constipation (IBS-C) is constipation in which gastrointestinal symptom dominated by abdominal pain, abdominal discomfort and stool abnormality is continued without organic changes in the gastrointestinal tract, and is included in the above functional constipation.

The diagnosis for functional constipation can be also measured for example by Rome III Diagnostic Criteria (see Non-patent literature 3, in specific p. 1486).

The diagnosis for IBS-C can be also measured for example by said Rome III Diagnostic Criteria (see Non-patent literature 3, in specific p. 1481-1482).

The pharmaceuticals of the present invention can improve one or two or more of the symptoms of constipation (frequency of bowel movements, sensation of incomplete evacuation, straining, stool form, abdominal bloating, abdominal discomfort and so on).

EXAMPLE

The present invention is further illustrated in more detail by way of the following Examples. However, the present invention is not limited thereto.

Example 1

Improvement Effect in Constipation Model 1

1. Preparation Procedure of Dosing Solution
(1) Preparation Procedure of Test Compounds Compound 2 was weighed and was dissolved in distilled water at preparation concentrations of 0.5, 1.5 and 5 mg/mL to prepare test compounds.

(2) Preparation Procedure of Control Substances

Lubiprostone (TLC Pharma Chem) was weighed and was suspended in 0.5% methylcellulose at preparation concentrations of 0.05 and 0.35 mg/mL to prepare control substances.

(3) Preparation Procedure of Reagent for Preparing the Model

Loperamide hydrochloride (Wako pure chemical) was weighed at 0.3, 0.5, 1.0, 2.0, 4.0 or 8.0 mg/kg for each animal and was filled into a gelatin capsule.

(4) Preparation Procedure of a Solution of Mixed Carbohydrate

A soluble starch, sucrose and lactose monohydrate were weighed at a rate of 6:3:1 and were dissolved in distilled water which was approximately 80% of the amounts of preparation on heating, and then the mixture was added with distilled water to prepare 0.4 g/mL solution of mixed carbohydrate.

2. Method
(1) Loperamide-Induced Dog Constipation Model

Loperamide hydrochloride which was filled into a gelatin capsule was orally administered to dogs (beagle, male, 13-14 months old, 10 dogs, Kitayama-labesu). The dosage was increased from 0.3 mg/kg, and was set at 2.0, 4.0 or 8.0 mg/kg based on the bowel movement condition of each dog. Dogs whose wet fecal weights during 24 hours after the administration of loperamide hydrochloride were significantly lower than the wet fecal weight during 24 hours of the non-treated dogs (Normal group) (fecal weight after administration<(average fecal weight without administration−2× standard deviation)) were subjected to the tests as constipation model animals.

(2) Experimental Procedure

Tests were performed as a full cross-over trial. More than 5-day washout period was provided between each test, and a recovery of stool form was identified, and then the next test was performed.

A gelatin capsule which was filled with loperamide hydrochloride was administered orally at around 9 a.m. on the first and second days in each test.

Compound 2 (1 mg/kg, 3 mg/kg or 10 mg/kg), lubiprostone (0.1 mg/kg or 0.7 mg/kg) or distilled water (2 mL/kg) was administered orally at around 4 p.m. on the second day using a glass syringe and an oral catheter, and then 0.4 g/mL solution of mixed carbohydrate was administered orally at 50 mL/body. The feces were observed at 17 hours, 21 hours and 24 hours after the administration, and the feces within 24 hours after the administration were collected and weighed, and it was set as the wet fecal weight. With regard to the frequency of bowel movement, it was counted as one bowel movement when the feces were observed at each observation point regardless of the size of the fecal volume. The stool form of feces was scored in seven categories based on Bristol Stool Form Scale. The collected feces were dried fully, and then the feces were weighed, and it was set as the dry fecal weight.

(3) Data Processing

The statistical analysis was made by testing the uniformity of variance using Bartlett's method, and multiple comparison between the group which was given distilled water (Control group) and each administered group was made using Dunnett's method when variance was uniform, and multiple comparison was made using Steel's method when variance was not uniform. In each case, significance level<5% was considered as significant difference.

3. Result

The data obtained from the tests were evaluated statistically. The means of wet fecal weights, dry fecal weights and frequencies of bowel movements within 24 hours after the administration of 10 subjects in each group are shown in Tables 1-3 and FIG. 1. Both Compound 2 and lubiprostone dose-dependently increased the wet fecal weight (Table 1), dry weight (Table 2) and frequency of bowel movements (Table 3 and FIG. 1), and these effects in the group administered with 3 mg/kg or more of Compound 2 and 0.1 mg/kg or more of lubiprostone were significantly higher than in Control group. In this test, increases of loose stool and diarrhea were not observed.

It was suggested that Compound 2 had the effects of increasing the fecal volume and the frequency of bowel movement in constipation model, and was useful as an agent for the prevention or treatment of constipation from the result of Example 1.

TABLE 1

Wet fecal weight within 24 hours after the administration

| Group | Wet fecal weight (g) |
| --- | --- |
| Normal group (non-treated) | 136.2 |
| Control group (distilled water) | 2.8 |
| The group administered with 1 mg/kg of Compound 2 | 29.5 |
| The group administered with 3 mg/kg of Compound 2 | 60.9 |
| The group administered with 10 mg/kg of Compound 2 | 77.2 |
| The group administered with 0.1 mg/kg of lubiprostone | 18.7 |
| The group administered with 0.7 mg/kg of lubiprostone | 55.4 |

TABLE 2

Dry fecal weight within 24 hours after the administration

| Group | Dry fecal weight (g) |
| --- | --- |
| Normal group (non-treated) | 47.1 |
| Control group (distilled water) | 1.0 |
| The group administered with 1 mg/kg of Compound 2 | 10.4 |
| The group administered with 3 mg/kg of Compound 2 | 21.6 |
| The group administered with 10 mg/kg of Compound 2 | 27.3 |
| The group administered with 0.1 mg/kg of lubiprostone | 8.3 |
| The group administered with 0.7 mg/kg of lubiprostone | 21.5 |

TABLE 3

Frequency of bowel movement within 24 hours after the administration

| Group | Frequency of bowel movement (time) |
| --- | --- |
| Normal group (non-treated) | 2.1 |
| Control group (distilled water) | 0.2 |
| The group administered with 1 mg/kg of Compound 2 | 0.5 |
| The group administered with 3 mg/kg of Compound 2 | 1.2 |
| The group administered with 10 mg/kg of Compound 2 | 1.5 |
| The group administered with 0.1 mg/kg of lubiprostone | 0.9 |
| The group administered with 0.7 mg/kg of lubiprostone | 1.0 |

Example 2

Improvement Effect in Constipation Model 2

1. Preparation Procedure of Dosing Solution
(1) Preparation Procedure of Test Compounds Compound 2 was weighed and was dissolved in distilled water at preparation concentrations of 3, 10 and 30 mg/mL as the free drug to prepare test compounds.

(2) Preparation Procedure of Control Substances 0.5% methylcellulose (0.5% MC) was used as a vehicle for preparation of lubiprostone. Lubiprostone was weighed and was suspended in 0.5% MC at preparation concentrations of 1, 3 and 10 mg/mL to prepare control substances.

(3) Preparation Procedure of a Positive Control Substance

Magnesium sulfate ($MgSO_4$) (Wako pure chemical) was weighed and was dissolved in distilled water at a preparation concentrations of 200 mg/mL to prepare a positive control substance.

(4) Preparation Procedure of a Solution of Mixed Carbohydrate

A soluble starch, sucrose and lactose monohydrate were weighed at a rate of 6:3:1 and were dissolved in distilled water which was approximately 80% of the amounts of preparation on heating, and then the mixture was added with distilled water to prepare 0.4 g/mL solution of mixed carbohydrate.

2. Low-Fiber Diet

A low-fiber diet was prepared based on the literature (Kakino et al. BMC Complementary and Alternative Medicine 2010, 10: 68).

3. Method (1) Preparation of a Rat Model of Low-Fiber Diet-Induced Constipation.

Rats were fed on the low-fiber diet for 1-2 weeks to induce constipation. Rats whose fecal weights during 24 hours were significantly lower than the fecal weight during 24 hours of the normal feed group (Normal group) (fecal volume when fed on the low-fiber diet<(average fecal volume of normal feed group−2× standard deviation)) were determined as constipation condition, and the rats which were fed on the low-fiber diet for 1 more week were subjected to the tests as a model of chronic constipation.

(3) Experimental Procedure

Compound 2 (3 mg/kg, 10 mg/kg or 30 mg/kg as free drug), lubiprostone (1 mg/kg, 3 mg/kg or 10 mg/kg), $MgSO_4$ (2000 mg/kg) or a vehicle (distilled water: Control group 1, 0.5% MC: Control group 2) was administered orally at around 9 a.m. using a 1 mL glass syringe and a stomach tube. Then, 0.4 g/mL solution of mixed carbohydrate was administered orally at 2 mL/body to Control group 1 and the groups administered with Compound 2. Distilled water was administered to the normal feed group. Test groups and the numbers of examples are shown in Table 4.

The feces were observed at 4, 8, 12 and 24 hours after the administration, and the feces were collected and weighed, and it was set as the fecal weight. The sum of the fecal weights at the collection times was set as the fecal weight at 24 hours after the administration.

TABLE 4

Test group and number of animal

| Test | Test group | Number of animal |
|---|---|---|
| (i) | Normal feed group | 4 |
| (ii) | Control group 1 | 4 |
| | The group administered with 3 mg/kg of Compound 2 | 4 |
| | The group administered with 10 mg/kg of Compound 2 | 4 |
| | The group administered with 30 mg/kg of Compound 2 | 4 |
| | The group administered with $MgSO_4$ | 4 |
| (iii) | Control group 2 | 5 |
| | The group administered with 1 mg/kg of lubiprostone | 5 |
| | The group administered with 3 mg/kg of lubiprostone | 5 |
| | The group administered with 10 mg/kg of lubiprostone | 5 |

(4) Data Processing

The statistical analysis was made by testing the uniformity of variance using Bartlett's method, and multiple comparison between Control group 1 and the group administered with Compound 2 or Control group 2 and the group administered with lubiprostone was made using Dunnett's method when variance was uniform respectively, and multiple comparison was made using Steel's method when variance was not uniform. In each case, significance level<5% was considered as significant difference.

4. Result

The combined and summarized data obtained from the normal feed group (i), the tests of Compound 2 and magnesium sulfate administration (ii) and the tests of lubiprostone administration (iii) are shown in Table 5.

Both Compound 2 and lubiprostone dose-dependently increased the fecal weight during 24 hours after the administration, and these effects in the groups administered with 10 mg/kg or more of Compound 2 and 10 mg/kg of lubiprostone were significantly higher than in each Control group. The increase of the fecal weight was also shown in the group administered with $MgSO_4$ which is a positive control. Moreover, watery stool was reported in the groups administered with 10 mg/kg or more of Compound 2, 3 mg/kg or more of lubiprostone and $MgSO_4$.

It was suggested that Compound 2 had the effects of increasing the fecal volume in constipation model, and was useful as an agent for the prevention or treatment of constipation from the result of Example 2.

TABLE 5

Fecal weight within 24 hours after the administration

| Test group | Fecal weight (g) |
|---|---|
| Normal feed group | 8.33 |
| Control group 1 | 0.53 |
| The group administered with 3 mg/kg of Compound 2 | 1.20 |
| The group administered with 10 mg/kg of Compound 2 | 4.20 |
| The group administered with 30 mg/kg of Compound 2 | 4.93 |
| The group administered with $MgSO_4$ | 3.70 |
| Control group 2 | 0.58 |
| The group administered with 1 mg/kg of lubiprostone | 0.60 |
| The group administered with 3 mg/kg of lubiprostone | 0.95 |
| The group administered with 10 mg/kg of lubiprostone | 1.25 |

Example 3

Single-Dose Study in Healthy Adult Males

1. Method

Compound 2 at a single dose of 2, 5, 10, 20, 40, 80 or 160 mg (free drug equivalent), or placebo was orally administered just immediately before breakfast to healthy adult males. For the administration of Compound 2, tablets containing 1, 5 or 10 mg in free drug equivalent were used. The test period was set between the administration and the discharge 48 hours after the administration. Frequencies of bowel movements were checked during consultation by a doctor, and the adverse events (gastrointestinal disorders) were defined when an abnormal finding (diarrhea or loose stool) was seen based on the stool form and the finding.

2. Result

In the groups administered with Compound 2, increases in the frequencies of bowel movement were observed (Table 6), and stool forms were determined at Bristol Stool Form Scale type 6 or 7 for many subjects in the 80 mg and 160 mg groups. Therefore, it was shown that Compound 2 made the stool soft and increased the frequency of bowel movement also in humans. The number of subjects with abdominal bloating, abdominal pain and diarrhea recoded as gastrointestinal disorders are shown in Table 7, but the severity was mild in all the cases.

TABLE 6

Frequency of bowel movement after the administration

| Dose | Compound 2 (mg) | | | | | | | Placebo |
|---|---|---|---|---|---|---|---|---|
| | 2 | 5 | 10 | 20 | 40 | 80 | 160 | |
| Number of subjects (subjects) | 6 | 6 | 6 | 6 | 6 | 6 | 6 | 14 |
| Mean (time) | 1.7 | 1.0 | 2.2 | 2.2 | 1.8 | 4.8 | 5.2 | 1.7 |
| SD | 0.8 | 0.9 | 1.2 | 0.8 | 1.7 | 3.5 | 1.2 | 1.1 |

TABLE 7

Number of subject with gastrointestinal disorders

| Dose | Compound 2 (mg) | | | | | | | Placebo |
|---|---|---|---|---|---|---|---|---|
| | 2 | 5 | 10 | 20 | 40 | 80 | 160 | |
| Number of subjects | 6 | 6 | 6 | 6 | 6 | 6 | 6 | 14 |
| Abdominal bloating | 0 | 0 | 0 | 0 | 0 | 2 | 3 | 0 |
| Abdominal pain | 0 | 0 | 0 | 0 | 0 | 4 | 3 | 0 |
| Diarrhea | 1 | 0 | 2 | 2 | 2 | 5 | 6 | 0 |

Example 4

Multiple-Dose Study in Healthy Adult Males

1. Method

Compound 2 at a dose of 2, 5, 10 or 20 mg (free drug equivalent), a placebo, or miglitol at a dose of 50 mg was repetitively administered orally once daily just immediately before breakfast on administration Days 1 and 13, and 3 times daily just immediately before every meal on administration Days 3 to 12 to healthy adult males. For the administration of Compound 2, tablets containing 1, 5 or 10 mg in free drug equivalent were used. The test period was set between administration Day 1 and Day 15. Frequencies of bowel movements were checked during consultation by a doctor, and the adverse events (gastrointestinal disorders) were defined when an abnormal finding (diarrhea or loose stool) was seen based on the stool form and the finding. In this regard, the frequencies of bowel movements in Table 8 show the daily means during fifteen days (time/day).

2. Result

There was a tendency of dose-dependent increase in the number of the subjects who had bowel movements with Bristol Stool Form Scale type 6 or type 7 and in the frequency thereof. The numbers of the subjects with diarrhea and abdominal pain recoded as gastrointestinal disorders are shown in Table 9. However, the severity of each subject was mild and the disorders disappeared or recovered without treatment.

TABLE 8

Daily frequency of bowel movement after the administration

| Dose | Compound 2 (mg) | | | | Placebo | Miglitol |
|---|---|---|---|---|---|---|
| | 2 | 5 | 10 | 20 | | |
| Number of subjects (subjects) | 8 | 8 | 8 | 8 | 8 | 8 |
| Mean (time/day) | 1.4 | 1.1 | 2.0 | 1.7 | 1.0 | 1.0 |
| SD | 0.6 | 0.5 | 1.2 | 1.0 | 0.4 | 0.4 |

TABLE 9

Number of subject with gastrointestinal disorders

| Dose | Compound 2 (mg) | | | | Placebo | Miglitol |
|---|---|---|---|---|---|---|
| | 2 | 5 | 10 | 20 | | |
| Number of subjects | 8 | 8 | 8 | 8 | 8 | 8 |
| Diarrhea | 6 | 5 | 5 | 6 | 3 | 2 |
| Abdominal pain | 0 | 0 | 0 | 1 | 0 | 0 |

Example 5

Clinical Trial in Patients with Chronic Constipation

1. Method

After observation for 2 weeks, Compound 2 or a placebo was administered orally after eating to 79 patients with chronic constipation for 4 weeks. Patients who had steady symptoms for long periods were selected as constipation patients using diagnostic criteria of functional constipation based on Rome III as a reference.

Each administered group is as follows:

2 mg TID group: administration of 2 mg of Compound 2, 3 times daily (after breakfast, after lunch, after dinner)

20 mg QD group: administration of 20 mg of Compound 2, 1 time daily (after breakfast)

20 mg BID group: administration of 20 mg of Compound 2, 2 times daily (after breakfast, after dinner)

20 mg TID group: administration of 20 mg of Compound 2, 3 times daily (after breakfast, after lunch, after dinner)

Placebo group: administration of placebo, 3 times daily (after breakfast, after lunch, after dinner)

For the administration of Compound 2, tablets containing 1 or 10 mg in free drug equivalent of Compound 2 were used.

If the subjects complained that further administration of 2 tablets each time was difficult due to the increase in the frequency of spontaneous bowel movements or softened stool form causing problems in daily life, the dose was switched to 1 tablet each time in the week 1 visit or week 2 visit by the doctor and the administration was continued.

2. Evaluation Items

Frequency of spontaneous bowel movements, frequency of complete bowel movements (frequency of spontaneous bowel movements without sensation of incomplete evacuation), percentage of patients who had a bowel movement within 24 hours after the first administration, percentage of patients who had a bowel movement within 48 hours after the first administration, time until the first spontaneous bowel movement, stool form (Bristol Stool Form Scale) and so on were evaluated.

3. Result (1) Subject 1

It was shown that the frequencies of spontaneous bowel movements per week of the subject 1 who was given 2 mg of Compound 2, 3 times daily (2 mg TID group) were 1.1, 7.0, 7.0, 11.0 and 10.5 (time/week) during the observation period, administration week 1, week 2, week 3 and week 4, respectively.

In addition, it was shown that the Bristol Stool Form Scales of the subject 1 were 1.5, 3.7, 3.7, 4.1 and 3.8 (mean/week) during the observation period, administration week 1, week 2, week 3 and week 4, respectively.

Also, the time until the first bowel movement was 5 hours and 20 minutes.

(2) Subject 2

It was shown that the frequencies of spontaneous bowel movements per week of the subject 2 who was given 20 mg of Compound 2, 1 time daily (20 mg QD group) were 1.8, 12.0, 13.0 and 8.0 (time/week) during the observation period, administration week 1, week 2 and week 3, respectively.

In addition, it was shown that the Bristol Stool Form Scales of the subject 2 were 3.0, 4.6, 4.0 and 3.4 (mean/week) during the observation period, administration week 1, week 2 and week 3, respectively.

Also, the the time until the first bowel movement was 24 hours and 20 minutes.

(3) Subject 3

It was shown that the frequencies of spontaneous bowel movements per week of the subject 3 who was given 20 mg of Compound 2, 2 times daily (20 mg BID group) and whose dose was then switched to 10 mg of Compound 2, 2 times daily at the day after the 1-week administration were 2.2, 21.0, 6.0, 6.0 and 5.0 (time/week) during the observation period, administration week 1, week 2, week 3 and week 4, respectively.

In addition, it was shown that the Bristol Stool Form Scales of the subject 3 were 2.0, 5.9, 4.0, 4.3 and 4.2 (mean/week) during the observation period, administration week 1, week 2, week 3 and week 4, respectively.

Also, the the time until the first bowel movement was 1 hour and 20 minutes.

It was shown that Compound 2 facilitated the spontaneous bowel movements and had an improvement effect on the stool form in patients with chronic constipation, and was useful as an agent for the treatment of chronic constipation from the result of Example 5. In this regard, no subjects with hypoglycemia were reported in the groups administered with Compound 2.

INDUSTRIAL APPLICABILITY

The pharmaceuticals of the present invention are very useful for the prevention or treatment of constipation.

The invention claimed is:

1. A method for the treatment of constipation, comprising administering to a patient in need thereof a pharmaceutical composition comprising as an active ingredient 3-(3-{4-[3-(β-D-glucopyranosyloxy)-5-isopropyl-1H-pyrazol-4-ylmethyl]-3-methylphenoxy}propylamino)-2,2-dimethylpropionamide, or a pharmaceutically acceptable salt thereof, and an appropriate pharmaceutical carrier, wherein a daily dose is 1 to 60 mg of 3-(3-{4-[3-(β-D-glucopyranosyloxy)-5-isopropyl-1H-pyrazol-4-ylmethyl]-3-methylphenoxy}propylamino)-2,2-dimethylpropionamide.

2. The method for the treatment of constipation as claimed in claim 1, wherein the active ingredient is bis[3-(3-{4-[3-(β-D-glucopyranosyloxy)-5-isopropyl-1H-pyrazol-4-ylmethyl]-3-methylphenoxy}propylamino)-2,2-dimethylpropionamide]monosebacate.

3. The method for the treatment of constipation as claimed in claim 1, wherein the constipation is functional constipation.

4. The method for the treatment of constipation as claimed in claim 3, wherein the functional constipation is chronic idiopathic constipation.

5. The method for the treatment of constipation as claimed in claim 3, wherein the functional constipation is drug-induced constipation.

6. The method for the treatment of constipation as claimed in claim 2, wherein the constipation is functional constipation.

* * * * *